US008693632B2

(12) United States Patent
Allison

(10) Patent No.: US 8,693,632 B2
(45) Date of Patent: Apr. 8, 2014

(54) ADAPTIVE X-RAY CONTROL

(75) Inventor: John W. Allison, Los Altos, CA (US)

(73) Assignee: Accuray Incorporated, Sunnyvale, CA (US)

( * ) Notice: Subject to any disclaimer, the term of this patent is extended or adjusted under 35 U.S.C. 154(b) by 0 days.

(21) Appl. No.: 13/407,379

(22) Filed: Feb. 28, 2012

(65) Prior Publication Data

US 2012/0213333 A1    Aug. 23, 2012

Related U.S. Application Data

(63) Continuation of application No. 12/250,262, filed on Oct. 13, 2008, which is a continuation of application No. 11/354,411, filed on Feb. 14, 2006, now abandoned.

(51) Int. Cl.
*A61N 5/10*     (2006.01)
*H05G 1/38*     (2006.01)
*H05G 1/44*     (2006.01)

(52) U.S. Cl.
USPC ................................. 378/95; 378/65; 378/96

(58) Field of Classification Search
USPC .................... 378/4–20, 62–65, 69, 95–97; 600/425–429
See application file for complete search history.

(56) References Cited

U.S. PATENT DOCUMENTS

| | | | |
|---|---|---|---|
| 4,409,615 A | 10/1983 | McMann et al. | |
| 4,942,596 A | 7/1990 | Eberhard et al. | |
| 5,187,730 A | 2/1993 | Fujihara | |
| 5,204,533 A | 4/1993 | Simonet | |
| 5,205,289 A | 4/1993 | Hardey et al. | |
| 5,207,223 A | 5/1993 | Adler | |
| 5,230,338 A | 7/1993 | Allen et al. | |
| 5,319,696 A | 6/1994 | Abdel-Malek et al. | |
| 5,398,684 A | 3/1995 | Hardey et al. | |
| 5,427,097 A | 6/1995 | Depp | |
| 5,471,516 A | 11/1995 | Nunan | |
| 5,724,403 A | 3/1998 | Siochi et al. | |
| 5,917,883 A | 6/1999 | Khutoryansky et al. | |
| 6,148,060 A | 11/2000 | Collins et al. | |
| 6,219,403 B1 * | 4/2001 | Nishihara | 378/65 |
| 6,385,286 B1 | 5/2002 | Fitchard et al. | |
| 6,504,893 B1 | 1/2003 | Flohr et al. | |
| 6,731,970 B2 | 5/2004 | Schlossbauer et al. | |
| 7,421,061 B2 | 9/2008 | Boese et al. | |
| 7,508,913 B2 | 3/2009 | Boese et al. | |

(Continued)

FOREIGN PATENT DOCUMENTS

EP    1332721 A1    8/2003
JP    2002058665    2/2002

(Continued)

OTHER PUBLICATIONS

Chen, Q-S. et al. (Sep. 2001). "Fluoroscopic Study of Tumor Motion due to Breathing: Facilitating Precise Radiation Therapy for Lung Cancer Patients", American Association of Physical Medicine, Medical Physics 28(9) 1850-1856.

PCT International Search Report and Written Opinion of the International Searching Authority, PCT/US07/04124, International Filing Date Feb. 13, 2007, mailed Mar. 4, 2008.

(Continued)

*Primary Examiner* — Anastasia Midkiff
(74) *Attorney, Agent, or Firm* — Lowenstein Sandler LLP

(57) ABSTRACT

Controlling the timing of acquiring x-ray images based on target movement.

13 Claims, 7 Drawing Sheets

(56) References Cited

U.S. PATENT DOCUMENTS

| | | | |
|---|---|---|---|
| 8,130,907 | B2 | 3/2012 | Maurer et al. |
| 2002/0085672 | A1 | 7/2002 | Ganin et al. |
| 2002/0191741 | A1 | 12/2002 | Brendler et al. |
| 2003/0048868 | A1 | 3/2003 | Bailey et al. |
| 2003/0215120 | A1 | 11/2003 | Uppaluri et al. |
| 2004/0044279 | A1 | 3/2004 | Lewin et al. |
| 2004/0092815 | A1 | 5/2004 | Schweikard et al. |
| 2004/0120452 | A1 * | 6/2004 | Shapiro et al. ............. 378/19 |
| 2005/0053196 | A1 | 3/2005 | Mostafavi |
| 2005/0058248 | A1 | 3/2005 | Klingenbeck-Regn |
| 2005/0201510 | A1 | 9/2005 | Mostafavi |
| 2005/0276377 | A1 | 12/2005 | Carol |
| 2006/0008174 | A1 | 1/2006 | Avinash et al. |
| 2006/0074292 | A1 | 4/2006 | Thomson et al. |
| 2006/0074299 | A1 | 4/2006 | Sayeh |
| 2006/0133573 | A1 | 6/2006 | Wong et al. |
| 2007/0015991 | A1 | 1/2007 | Fu et al. |
| 2007/0076846 | A1 * | 4/2007 | Ruchala et al. ............. 378/65 |
| 2007/0078306 | A1 | 4/2007 | Allison et al. |
| 2007/0100233 | A1 | 5/2007 | Thomson |
| 2007/0165781 | A1 | 7/2007 | Aslund |
| 2007/0189455 | A1 | 8/2007 | Allison |
| 2007/0270689 | A1 | 11/2007 | Lotbert |
| 2008/0031404 | A1 | 2/2008 | Khamene et al. |
| 2009/0041189 | A1 | 2/2009 | Allison |
| 2010/0067660 | A1 * | 3/2010 | Maurer et al. ............. 378/95 |
| 2012/0008734 | A1 * | 1/2012 | Thomson et al. ............. 378/4 |

FOREIGN PATENT DOCUMENTS

| | | | |
|---|---|---|---|
| JP | 2003245272 | | 9/2003 |
| JP | 2004166975 | | 6/2004 |
| WO | WO 9927839 | A2 * | 6/1999 |
| WO | 2004008969 | A2 | 1/2004 |

OTHER PUBLICATIONS

Coste-Maniere, E., "Robotic whole body stereotactic radiosurgery: clinical advantages of the CyberKnife® integrated system", The International Journal of Medical Robotics +Computer Assisted Surgery, 2005, www.robacpublicationsmm, 12 pages.

Penney, G.P. et al., "A Comparison of Similarity Measures for Use in 2-D—3-D Medical Image Registration", IEEE Transactions on Medical Imaging, vol. 17, No. 4, Aug. 1998, pp. 589-595.

Tapiovaara, M.J. et al., "Evaluation of Image Quality in Fluroscopy by Measurements and Monte Carlo Calculations", Phys. Med. Biol. 40 (1995) Copyright 1998IOP Publishing LTD, pp. 589-607.

PCT International Preliminary Report on Patentability, PCT/US2007/004124, International Filing Date Feb. 13, 2007, mailed Aug. 28, 2008.

Accuray Incorporated Office Action for U.S. Appl. No. 11/354,411 mailed May 14, 2009.

PCT International Search Report and The Written Opinion of the International Searching Authority, PCT/US09/05149, filed Sep. 11, 2009, mailed Nov. 9, 2009, 13 pages.

U.S. Appl. No. 12/250,262, Final Office Action mailed Dec. 1, 2009.

U.S. Appl. No. 12/250,262, Office Action mailed Apr. 22, 2010.

U.S. Appl. No. 12/250,262, Office Action mailed Dec. 8, 2010.

U.S. Appl. No. 12/250,262, Final Office Action mailed Jun. 13, 2011.

Non-final Office Action mailed Jun. 14, 2011, for U.S. Appl. No. 12/558,489, filed Sep. 9, 2011, 12 pages.

Notice of Allowance mailed Oct. 27, 2011, for U.S. Appl. No. 12/558,489, filed Sep. 9, 2011, 9 pages.

Communication dated Nov. 26, 2010 for European patent application No. 07750926.3-2319, 3 pages.

European Search Report, EP07750926 dated Feb. 28, 2011, 8 pages.

First Notification of Office Action, Chinese Patent Application No. 200780005551.5, Date of Issue: Jun. 23, 2010.

European Search Report EP09813381.2, mailed Jan. 24, 2013, 5 pages.

U.S. Appl. No. 13/359,365, Office Action mailed Sep. 26, 2013.

* cited by examiner

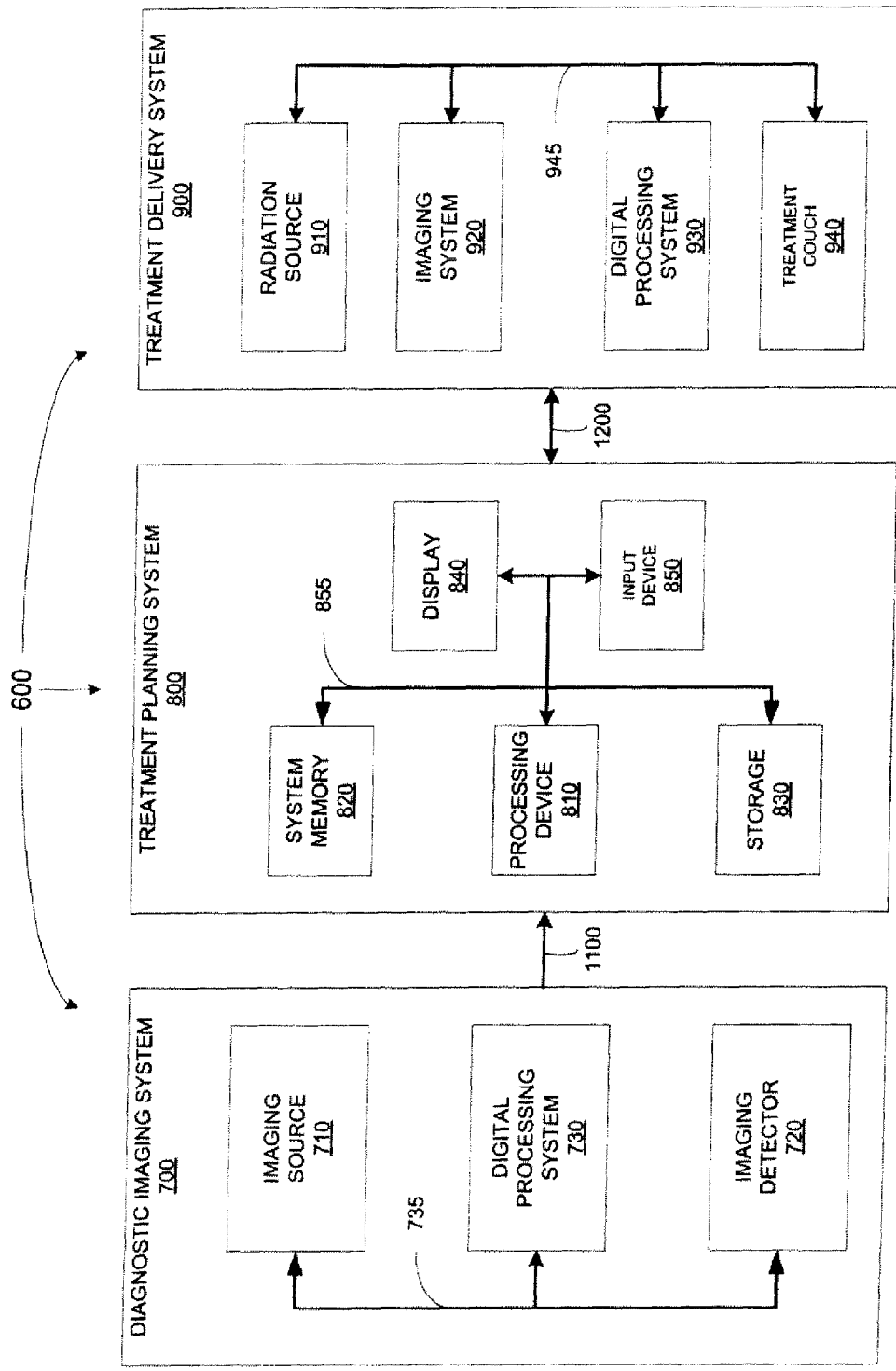

ADAPTIVE X-RAY CONTROL

REFERENCE TO RELATED APPLICATION

This application is a continuation of U.S. patent application Ser. No. 12/250,262, filed Oct. 13, 2008, which is a continuation of U.S. patent application Ser. No. 11/354,411, filed Feb. 14, 2006, both of which are hereby incorporated by reference herein.

TECHNICAL FIELD

Embodiments of the invention relate to medical imaging and, in particular, to the control of x-ray exposure during medical imaging.

BACKGROUND

Radiosurgery and radiotherapy systems are radiation treatment systems that use external radiation beams to treat pathological anatomies (e.g., tumors, lesions, vascular malformations, nerve disorders, etc.) by delivering a prescribed dose of radiation (e.g., x-rays or gamma rays) to the pathological anatomy while minimizing radiation exposure to surrounding tissue and critical anatomical structures (e.g., the spinal chord). Both radiosurgery and radiotherapy are designed to necrotize the pathological anatomy while sparing healthy tissue and the critical structures. Radiotherapy is characterized by a low radiation dose per treatment, and many treatments (e.g., 30 to 45 days of treatment). Radiosurgery is characterized by a relatively high radiation dose in one, or at most a few, treatments.

In both radiotherapy and radiosurgery, the radiation dose is delivered to the site of the pathological anatomy from multiple angles. As the angle of each radiation beam is different, each beam can intersect a target region occupied by the pathological anatomy, while passing through different regions of healthy tissue on its way to and from the target region. As a result, the cumulative radiation dose in the target region is high and the average radiation dose to healthy tissue and critical structures is low. Radiotherapy and radiosurgery treatment systems can be classified as frame-based or image-guided.

In frame-based radiosurgery and radiotherapy, a rigid and invasive frame is fixed to the patient to immobilize the patient throughout a diagnostic imaging and treatment planning phase, and a subsequent treatment delivery phase. The frame is fixed on the patient during the entire process. Image-guided radiosurgery and radiotherapy (IGR) eliminate the need for invasive frame fixation by tracking and correcting for patient movement during treatment.

Image-guided radiotherapy and radiosurgery systems include gantry-based systems and robotic-based systems. In gantry-based systems, the radiation source is attached to a gantry that moves around a center of rotation (isocenter) in a single plane. Each time a radiation beam is delivered during treatment, the axis of the beam passes through the isocenter. In some gantry-based systems, known as intensity modulated radiation therapy (IMRT) systems, the cross-section of the beam is shaped to conform the beam to the pathological anatomy under treatment. In robotic-based systems, the radiation source is not constrained to a single plane of rotation.

In image-guided systems, patient tracking during treatment is accomplished by registering two-dimensional (2-D) intra-treatment x-ray images of the patient (indicating where the patient is) to 2-D reference projections of one or more pre-treatment three-dimensional (3-D) volume studies of the patient (indicating where the patient should be to match the treatment plan). The pre-treatment 3-D volume studies may be computed tomography (CT) scans, magnetic resonance imaging (MRI) scans, positron emission tomography (PET) scans or the like.

The reference projections (reference images), known as digitally reconstructed radiographs (DRRs) are generated using ray-tracing algorithms that replicate the geometry of the intra-treatment x-ray imaging system to produce images that have the same scale as the intra-treatment x-ray images. Typically, the intra-treatment x-ray system is stereoscopic, producing images of the patient from two different points of view (e.g., orthogonal views).

As x-ray imaging technology advances, the sensitivity of the x-ray detectors used to capture the intra-treatment x-ray images is increasing. These increases are due, at least in part, to improved imaging materials (e.g., amorphous silicon) and image capture technologies (e.g., CCD and CMOS imaging arrays) and processing algorithms which reduce the quantum noise and electronic noise levels of the x-ray detectors and increase the signal-to-noise ratios of the intra-treatment x-ray images for any given imaging radiation level. Generally, a higher signal-to-noise ratio produces higher quality images that translate to improvements in image registration and patient tracking due to improved detectability of anatomical features and/or fiducial markers. For any given noise figure, the detectability of an anatomical object can be improved by changing x-ray properties. Two such changes can involve increasing the imaging radiation dose or energy to increase the SNR. FIG. 1 illustrates the improved detectability of an anatomical object 10 in a field of view 20 as the SNR is increased from 1:1 to 2:1 to 5:1 as the radiation dose is increased. X-ray sources used to generate intra-treatment x-ray images are typically set to dose and energy levels sufficient to penetrate larger patients and provide the required x-ray image quality (SNR level) for consistent and reliable tracking of patient and anatomical motion during setup and treatment. However, above a certain minimum SNR (e.g., 1:1), improvements in patient tracking and image registration may be offset by increased risks to the patient from higher radiation doses.

BRIEF DESCRIPTION OF THE DRAWINGS

Embodiments of the present invention are illustrated by way of example, and not by limitation, in the figures of the accompanying drawings in which:

FIG. 6 illustrates a system in which embodiments of the present invention may be practiced.

DETAILED DESCRIPTION

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention.

The term "coupled" as used herein, may mean directly coupled or indirectly coupled through one or more intervening components or systems. The term "x-ray image" as used herein may mean a visible x-ray image (e.g., displayed on a video screen) or a digital representation of an x-ray image (e.g., a file corresponding to the pixel output of an x-ray detector). The term "intra-treatment x-ray image" as used herein may refer to images captured at any point in time during the patient setup or treatment delivery phase of a radiosurgery or radiotherapy procedure, which may include times when the radiation treatment source is either on or off. Reference to an "x-ray image" may refer to a single image or a simultaneous or consecutive pair of images (as in a stereoscopic imaging system as described above). The term "IGR" as used herein may refer to image-guided radiotherapy, image-guided radiosurgery or both. A "target" as discussed herein may be an anatomical feature(s) of a patient such as a pathological anatomy (e.g., tumor, lesion, vascular malformation, nerve disorder, etc.) or normal anatomy and may include one or more non-anatomical reference structures.

Unless stated otherwise as apparent from the following discussion, it will be appreciated that terms such as "processing," "computing," "determining," "estimating," "acquiring," "generating" or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage, transmission or display devices. Embodiments of the method described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

Figure 1:
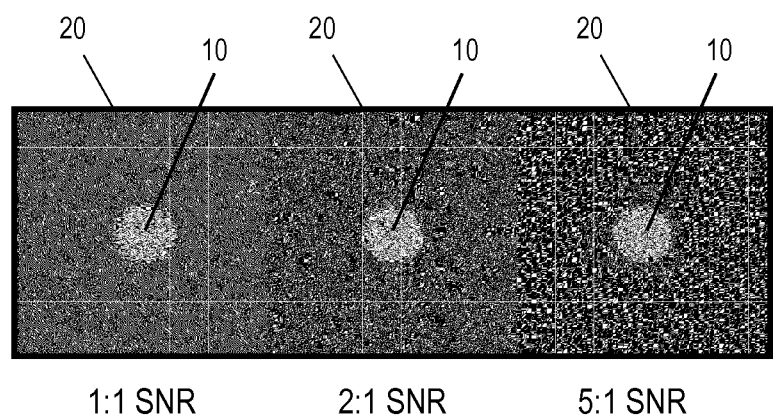
FIG. 1 illustrates x-ray detection as a function of signal to noise ratio.
Figure 2A:
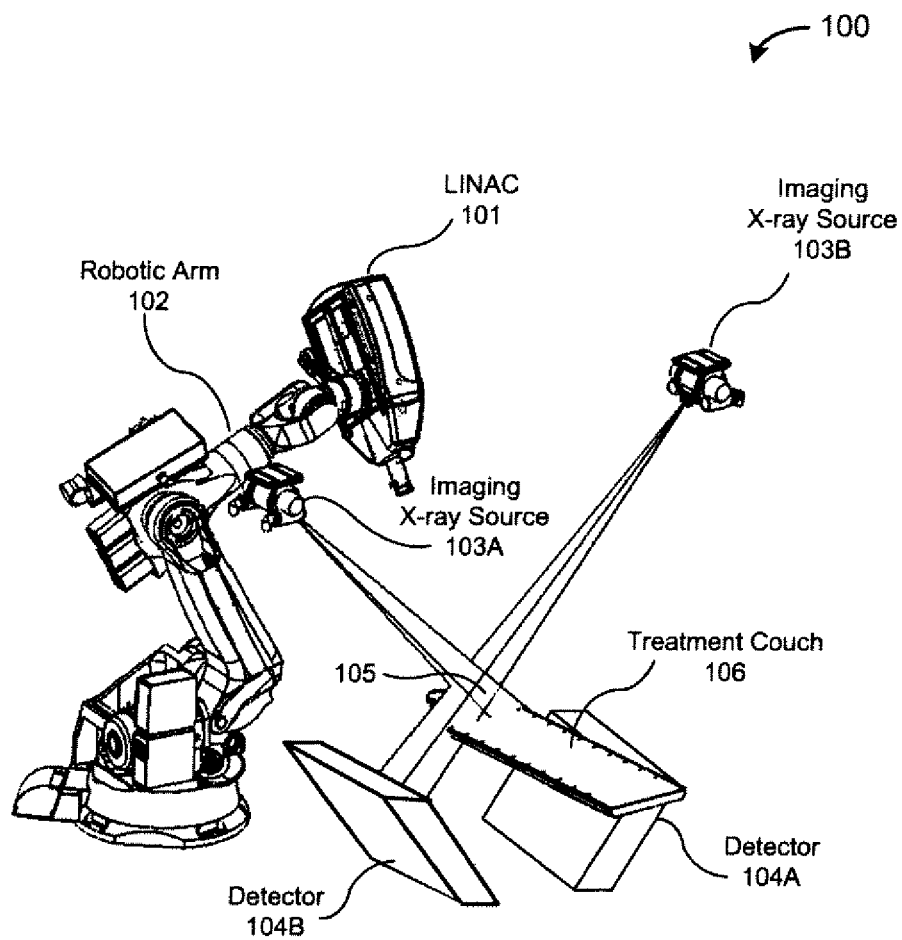
FIG. 2A illustrates an image-guided robotic radiosurgery system in one embodiment.
Figure 2B:
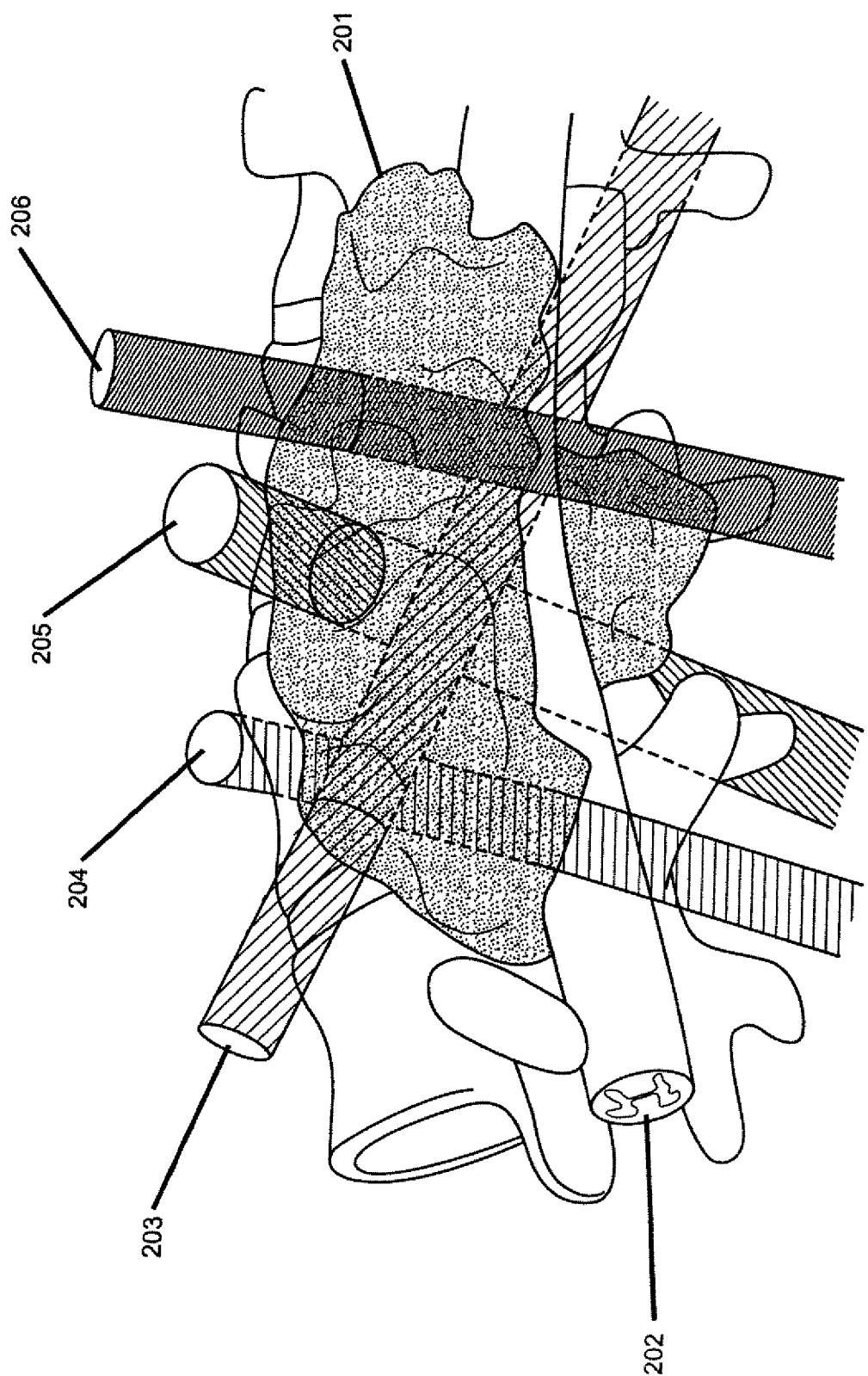
FIG. 2B illustrates non-isocentric radiation treatment in one embodiment of an image-guided radiosurgery system.

FIG. 2A illustrates the configuration of an image-guided, robotic-based radiation treatment system 100, such as the CyberKnife® Radiosurgery System manufactured by Accuray, Inc. of California. In FIG. 2A, the radiation treatment source is a linear accelerator (LINAC) 101 mounted on the end of a robotic arm 102 having multiple (e.g., 5 or more) degrees of freedom in order to position the LINAC 101 to irradiate a pathological anatomy (target region or volume) with beams delivered from many angles, in many planes, in an operating volume around the patient. Treatment may involve beam paths with a single isocenter, multiple isocenters, or with a non-isocentric approach. FIG. 2B illustrates non-isocentric radiation treatment in one embodiment. In FIG. 2B, a pathological anatomy (e.g., a tumor) 201 growing around a spinal cord (202) is treated for example, by radiation treatment beams 203, 204, 205 and 206, which each intersect the pathological target volume without converging on a single point, or isocenter, within the target).

In FIG. 2A, the imaging system may include x-ray sources 103A and 103B and x-ray detectors 104A and 104B. The two x-ray sources 103A and 103B may be mounted in fixed positions on the ceiling of an operating room and may be aligned to project imaging x-ray beams from two different angular positions (e.g., separated by 90 degrees) to intersect at a machine isocenter 105 (which provides a reference point for positioning the patient on a treatment couch 106 during treatment) and to illuminate imaging planes of respective x-ray detectors 104A and 104B after passing through the patient. In other embodiments, system 100 may include more than two x-ray sources and more than two x-ray detectors, and any of the x-ray sources and x-ray detectors may be movable rather than fixed. In yet other embodiments, the positions of the x-ray sources and the x-ray detectors may be interchanged or located on opposing walls.

The x-ray detectors 104A and 104B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with the reference images during the registration process.

As noted above, the imaging radiation levels (output levels) of conventional systems may be based on worst-case assumptions about imaging conditions. In one embodiment of the invention, the output levels of the x-ray sources (e.g., sources 103A and 103B) may be independently adapted to actual imaging conditions and actual signal-to-noise ratios to generate x-ray images with signal-to-noise ratios that are high enough for adequate patient tracking performance while minimizing a patient's x-ray exposure during setup and treatment. Initially, the x-ray sources may be set to a nominal output level based, for example, on a worst case assumption regarding signal attenuation through the patient or estimated from patient physiological data (e.g., weight). Alternatively, the output level may be estimated using attenuation data from a pre-treatment diagnostic x-ray study of the patient (e.g., a CT scan). The SNR of an x-ray image and/or images thus acquired may be measured (see, e.g., M. J. Tapiovaara & M. Sandborg, *Evaluation of Image Quality in Flouroscopy by Measurements and Monte Carlo Calculations,* 40 Phys. Med. Biol. 589-607 (1995)) and used for adaptively controlling subsequent x-ray image acquisitions. The x-ray radiation properties can be optimized for each source and detector pair separately to achieve satisfactory imaging performance while minimizing x-ray radiation exposure to the patient during setup and treatment.

Figure 3:
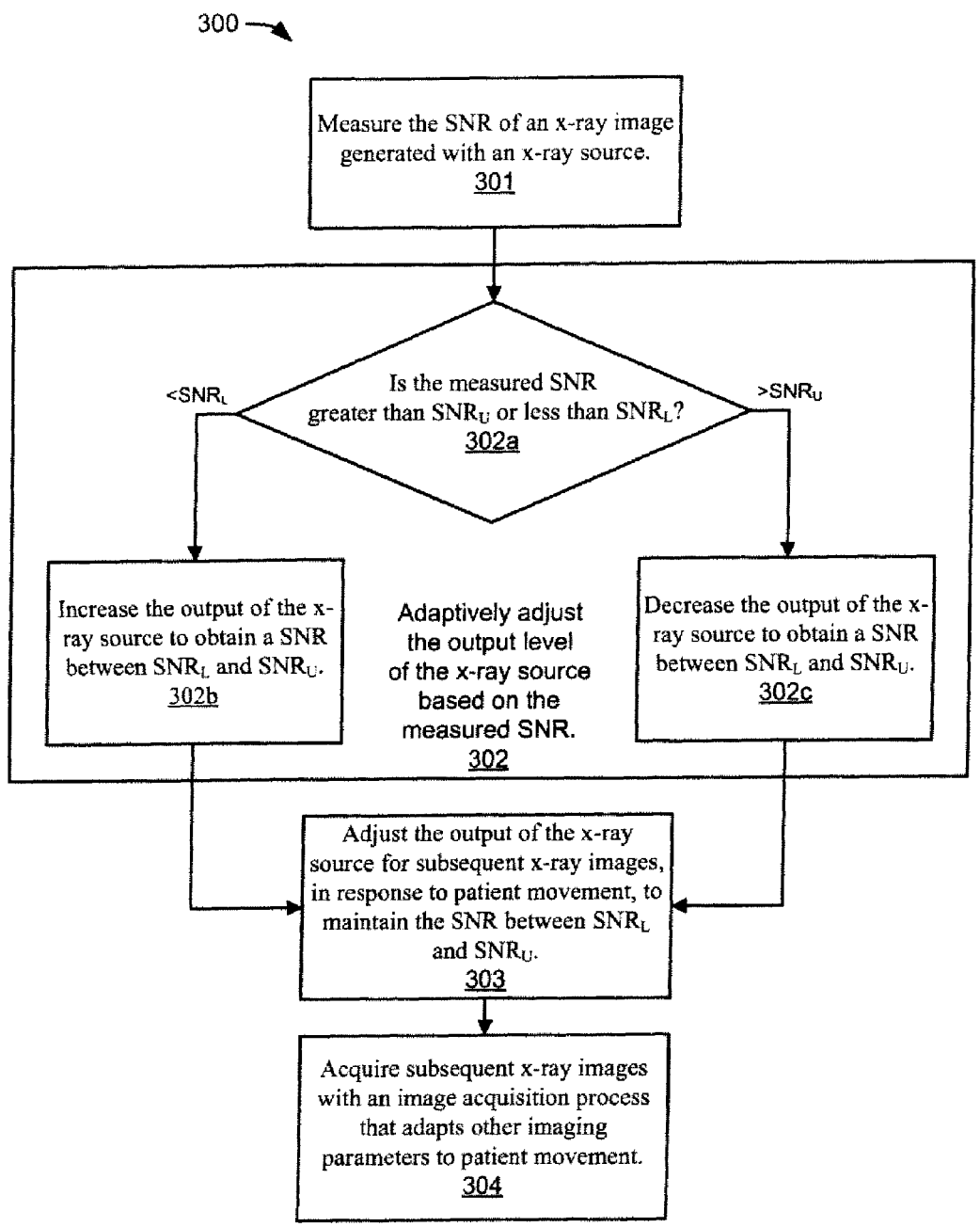
FIG. 3 is a flowchart illustrating a method in one embodiment of adaptive x-ray control.

FIG. 3 illustrates a method of adaptive x-ray control 300 in one embodiment of the invention. As illustrated in FIG. 3, the method may include measuring the SNR of an x-ray image generated with an x-ray source (e.g., x-ray source such as x-ray sources 103A, 103B) using an initial output value as described above (step 301). Then, the method may adaptively adjust the output level of the x-ray source, based on the measured SNR (step 302). In one embodiment, step 302 may include comparing the measured SNR with a predetermined lower SNR threshold ($SNR_L$) required for reliable patient tracking, and with a predetermined upper SNR threshold ($SNR_U$) (step 302a). If the measured SNR ratio is less than $SNR_L$, then the method increases the output of the x-ray source to obtain a SNR between $SNR_U$ and $SNR_L$ (step 302b). If the measured SNR is greater than $SNR_U$, then the method decreases the output of the x-ray source to obtain a SNR between $SNR_U$ and $SNR_L$ (step 302c). If the measured SNR is between $SNR_U$ and $SNR_L$, then no change in x-ray output (or imaging parameter) is made. The output of an x-ray source may include both an energy level and an exposure duration (on-time), and one or both parameters may be increased or decreased to adjust the output of the x-ray source. In one embodiment, as described in greater detail below, the method may also include adjusting the output of the x-ray source for subsequent x-ray images, in response to patient movement, to maintain a SNR between $SNR_U$ and $SNR_L$. (step 303). In other embodiments, described in greater detail below, subsequent x-ray images may be acquired with an image acquisition process that adapts to patient movement (step 304). Other embodiments include apparatus, systems and articles of manufacture capable of performing the method, described in greater detail below.

If the measured SNR is below $SNR_L$ or above $SNR_U$, the system may notify the operator of the image-guided radiation treatment system and may request the operator to increase or decrease the output of the x-ray source to obtain a SNR within the desired SNR range. Alternatively, the adjustments to the output may be made automatically by the system (e.g., using closed-loop feedback as is known in the art) without operator intervention. The adjustment of the output of the x-ray source, as described above, may be implemented throughout a radiation treatment session in response to changes in imaging conditions due to changes in patient position resulting from intentional patient repositioning (e.g., as part of the treatment plan) or from unplanned movement initiated by the patient. Other imaging parameters may also be adjusted in response to patient movement. For example, time intervals between subsequent x-rays as well as the number of x-rays may be adjusted in response to patient movement as described in greater detail below.

Figure 4:
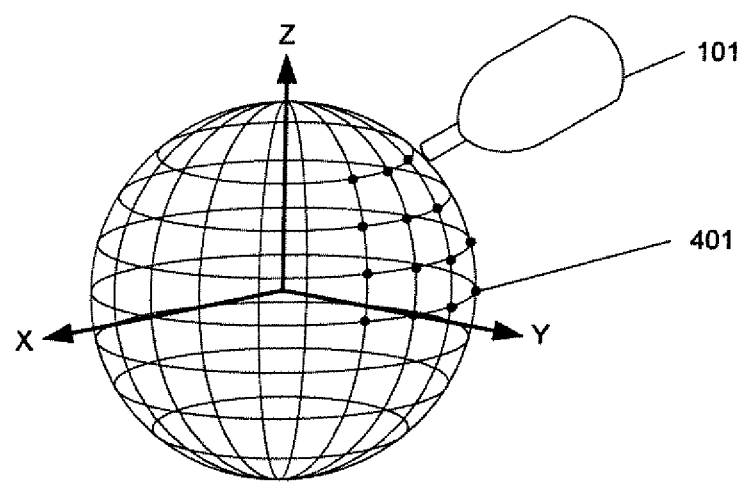
FIG. 4 illustrates treatment nodes in one embodiment of adaptive x-ray control.

A radiation treatment plan, as described above, may include the application of radiation treatment beams to the pathological anatomy from a number of treatment nodes, with one or more beams being applied from each node. FIG. 4 illustrates how LINAC 101 may be positioned at a node 401, which may be part of an approximately spherical distribution of nodes, for example, such as node 401. The particular number of nodes and the number of treatment beams applied at each node may vary as a function of the location and type of pathological anatomy (for example, the number of nodes may vary from 50 to 300 and the number of beams may vary from 200 to 1200), and may be determined during the treatment planning phase. A treatment plan may include target radiation doses to pathological anatomies (e.g., minimum doses) and to healthy tissues and structures (e.g., maximum doses). The total radiation dose received by a patient is the sum of the radiation dose from the treatment beams and the radiation dose from the imaging x-ray sources. Therefore, the treatment plan may set the total dose of the treatment beams (e.g., number, energy level and/or duration) to account for the radiation dose from the planned imaging x-ray exposure (e.g., number of images, energy level and duration).

In one embodiment, an initial treatment plan may call for x-ray images to be taken at fixed time intervals during the treatment (every two seconds, for example). The initial treatment plan may be based on an expected amount of patient movement, based for example on a statistically significant historical sample of patients undergoing the same or similar procedure. During treatment, patient movement may be detected by comparing two or more sequential x-ray images. Differences between the sequential images may be used to register a patient coordinate system with a treatment coordinate system to insure that the treatment beams are accurately positioned with respect to the pathological anatomy. Differences between the sequential images may be measured using methods known in the art such as feature recognition, pattern intensity matching and the like (see, e.g., G. P. Penney & J. Weese, *A Comparison of Similarity Measures for Use in 2D-3D Medical Image Registration*, 17 IEEE Trans. Med. Imag. 586-595, (1998)). If the differences between the sequential x-ray images indicate a small amount of patient movement that is well within treatment tolerances (small displacement and low displacement variance), the time intervals between subsequent x-ray images may be increased by the image acquisition process to reduce patient exposure to imaging x-rays. If the differences between the sequential x-ray images indicate a large amount of patient movement (large displacement and high displacement variance), the time intervals between subsequent x-ray images may be decreased by the image acquisition process.

Figure 5:
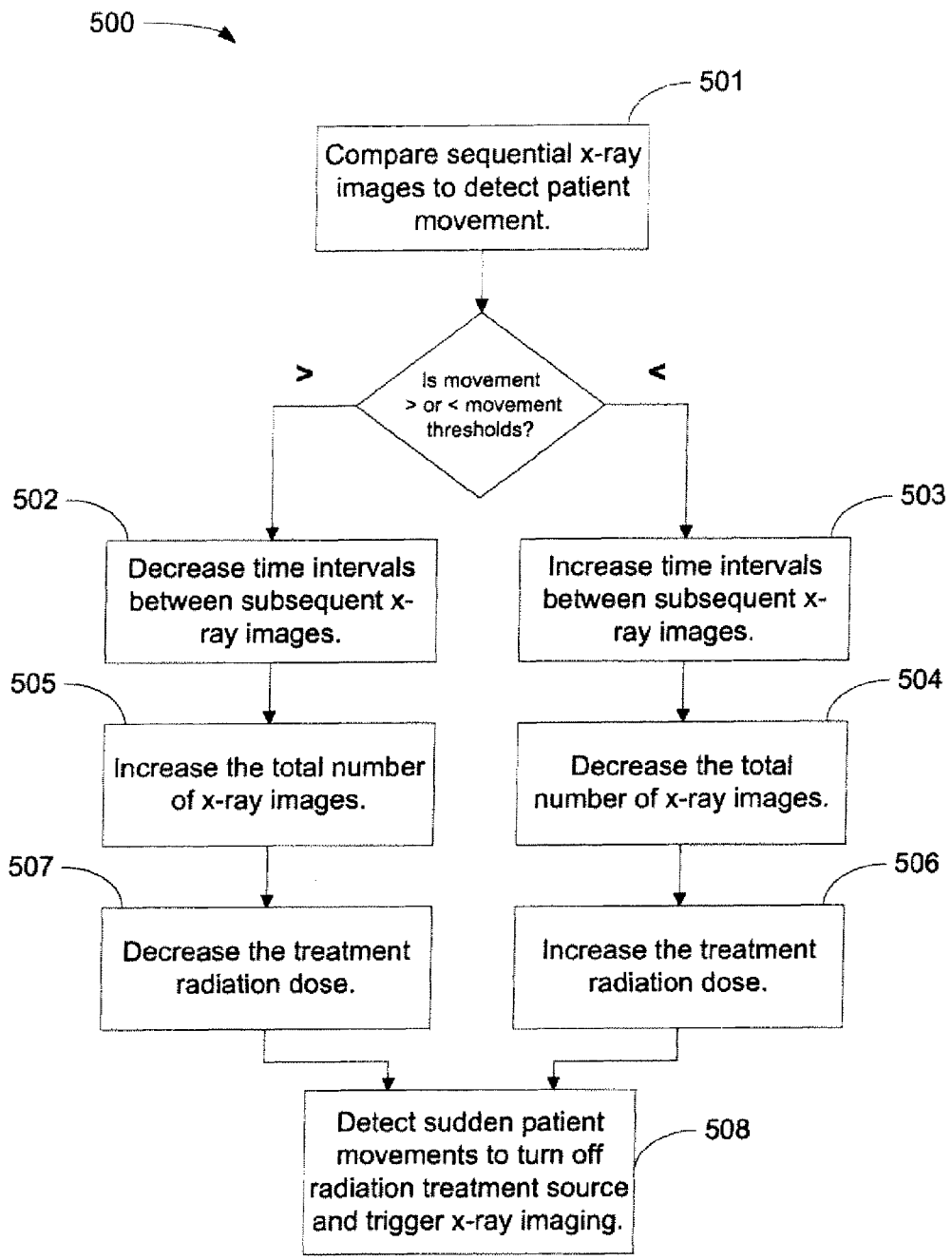
FIG. 5 is a flowchart illustrating a method in another embodiment of adaptive x-ray control.

FIG. 5 illustrates an imaging acquisition process 500, in one embodiment of step 304 of method 300 described above. The process begins by comparing sequential x-ray images to detect patient movement (step 501). Then, if the patient movement indicated by the differences between the sequential x-ray images is greater than a movement and/or movement variance threshold (movement thresholds), the time intervals between subsequent x-ray images may be decreased (step 502) to insure that any patient movement between subsequent x-ray images does not exceed a specified amount (e.g., a root mean square (RMS) displacement of 0.5 mm). However, if the patient movement indicated by the differences between the sequential x-ray images is less than the movement thresholds during that time interval, the time intervals between subsequent x-ray images may be increased (step 503).

In a given treatment plan having a planned number of x-ray images and a planned number of treatment nodes and/or treatment paths, the total treatment time will be determined by the time required to position and fire the radiation treatment source (e.g., LINAC 101) at each node. Increasing or decreasing the time intervals between sequential x-ray images will result in a difference between the planned treatment time and the planned imaging time. In one embodiment, therefore, the image acquisition process may include adjusting the total number of x-ray images in response to patient movement to maintain a correspondence between the treatment time and the imaging time. That is, the number of x-ray images per treatment node and/or treatment path (e.g., the ratio of x-ray images to treatment nodes and/or treatment paths) may be adjusted in response to patient movement. As illustrated in FIG. 5, the method 500 may include determining if the time intervals between subsequent x-ray images has been increased (step 503) or decreased (step 502) in response to patient movement. If the time intervals have been increased, then the total number of x-ray images may be decreased (step 504). If the time intervals have been decreased, then the total number of x-ray images may be increased (step 505).

For a given output level from an x-ray source, increasing the total number of x-ray images will increase the cumulative radiation exposure during the radiation treatment session. Conversely, decreasing the total number of x-ray images will decrease the cumulative radiation exposure during the radiation treatment session. In one embodiment, if the total number of x-ray images is decreased, the method 500 may include increasing the treatment radiation dose in the current or a future treatment session (treatment fraction) to compensate for the reduced imaging x-ray exposure and maintain a planned cumulative radiation exposure (step 506). If the total number of x-ray images is increased, then the method 500 may include decreasing the treatment radiation dose in the current or a future treatment fraction to compensate for the increased imaging x-ray exposure to maintain the planned cumulative radiation exposure (step 507).

Motion detection using sequential x-ray images to adjust radiation exposure, as described above, may not be sufficient to detect sudden patient movements such as those due to muscle twitches or spasms. For example, even if the frequency of the x-ray images is one per second, a cough or muscle twitch could cause enough movement in the patient to make the x-ray treatment beam miss its intended target. In one embodiment, the method 500 may include a step for detecting sudden movements, turning off the treatment x-ray source if the patient movement exceeds a specified rate and triggering a new x-ray image (step 508). Such a step may be implemented, for example, by monitoring the patient with a machine vision system or a strain gauge attached to the patient. Such monitoring methods are known in the art and, accordingly are not described in detail. In one embodiment, a scanning laser may continuously map and monitor the 3D patient surface. Comparisons of sequential scans can detect sudden movements that result in a significant displacement (e.g. >1 mm), suspend treatment delivery until patient and target alignment can be verified, and can trigger the x-ray image acquisition process. This approach permits a more aggressive reduction of image acquisition (as a function of time or treatment node) because significant changes in patient alignment will be detected in parallel with the sequential imaging method and trigger a new x-ray image acquisition to verify patient alignment before treatment can resume.

FIG. 6 illustrates one embodiment of systems that may be used in performing radiation treatment in which features of the present invention may be implemented. As described below and illustrated in FIG. 6, a system 600 may include a diagnostic imaging system 700, a treatment planning system 800 and a treatment delivery system 900.

Diagnostic imaging system 700 may be any system capable of producing medical diagnostic images of a patient that may be used for subsequent medical diagnosis, treatment planning and/or treatment delivery. For example, diagnostic imaging system 700 may be a computed tomography (CT) system, a magnetic resonance imaging (MRI) system, a positron emission tomography (PET) system, an ultrasound system or the like. For ease of discussion, diagnostic imaging system 700 may be discussed below at times in relation to a CT x-ray imaging modality. However, other imaging modalities such as those above may also be used.

Diagnostic imaging system 700 includes an imaging source 710 to generate an imaging beam (e.g., x-rays, ultrasonic waves, radio frequency waves, etc.) and an imaging detector 720 to detect and receive the beam generated by imaging source 710, or a secondary beam or emission stimulated by the beam from the imaging source (e.g., in an MRI or PET scan).

The imaging source 710 and the imaging detector 720 may be coupled to a digital processing system 730 to control the imaging operation and process image data. Diagnostic imaging system 700 includes a bus or other means 735 for transferring data and commands among digital processing system 730, imaging source 710 and imaging detector 720. Digital processing system 730 may include one or more general-purpose processors (e.g., a microprocessor), special purpose processor such as a digital signal processor (DSP) or other type of device such as a controller or field programmable gate array (FPGA). Digital processing system 730 may also include other components (not shown) such as memory, storage devices, network adapters and the like. Digital processing system 730 may be configured to generate digital diagnostic images in a standard format, such as the DICOM (Digital Imaging and Communications in Medicine) format, for example. In other embodiments, digital processing system 730 may generate other standard or non-standard digital image formats. Digital processing system 730 may transmit diagnostic image files (e.g., the aforementioned DICOM formatted files) to treatment planning system 800 over a data link 1100, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 800 includes a processing device 810 to receive and process image data. Processing device 810 may represent one or more general-purpose processors (e.g., a microprocessor), special purpose processor such as a digital signal processor (DSP) or other type of device such as a controller or field programmable gate array (FPGA). Processing device 810 may be configured to execute instructions for performing treatment planning operations discussed herein.

Treatment planning system 800 may also include system memory 820 that may include a random access memory (RAM), or other dynamic storage devices, coupled to processing device 810 by bus 855, for storing information and instructions to be executed by processing device 810. System memory 820 also may be used for storing temporary variables or other intermediate information during execution of instructions by processing device 810. System memory 820 may also include a read only memory (ROM) and/or other static storage device coupled to bus 855 for storing static information and instructions for processing device 810.

Treatment planning system 800 may also include storage device 830, representing one or more storage devices (e.g., a magnetic disk drive or optical disk drive) coupled to bus 855 for storing information and instructions. Storage device 830 may be used for storing instructions for performing the treatment planning steps discussed herein.

Processing device 810 may also be coupled to a display device 840, such as a cathode ray tube (CRT) or liquid crystal display (LCD), for displaying information (e.g., a 2D or 3D representation of the VOI) to the user. An input device 850, such as a keyboard, may be coupled to processing device 810 for communicating information and/or command selections to processing device 810. One or more other user input devices (e.g., a mouse, a trackball or cursor direction keys) may also be used to communicate directional information, to select commands for processing device 810 and to control cursor movements on display 840.

It will be appreciated that treatment planning system 800 represents only one example of a treatment planning system, which may have many different configurations and architectures, which may include more components or fewer components than treatment planning system 800 and which may be employed with the present invention. For example, some systems often have multiple buses, such as a peripheral bus, a dedicated cache bus, etc. The treatment planning system 800 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 800 may share its database (e.g., data stored in storage device 830) with a treatment delivery system, such as treatment delivery system 900, so that it may not be necessary to export from the treatment planning system prior to treatment delivery. Treatment planning system 800 may be linked to treatment delivery system 900 via a data link 1200, which may be a direct link, a LAN link or a WAN link as discussed above with respect to data link 1100. It should be noted that when data links 1100 and 1200 are implemented as LAN or WAN connections, any of diagnostic imaging system 700, treatment planning system 800 and/or treatment delivery system 900 may be in decentralized locations such that the systems may be physically remote from each other. Alternatively, any of diagnostic imaging system 700, treatment planning system 800 and/or treatment delivery system 900 may be integrated with each other in one or more systems.

Treatment delivery system 900 includes a therapeutic and/or surgical radiation source 910 to administer a prescribed radiation dose to a target volume in conformance with a treatment plan. Treatment delivery system 900 may also include an imaging system 920 to capture intra-treatment images of a patient volume (including the target volume) for registration or correlation with the diagnostic images described above in order to position the patient with respect to the radiation source. Imaging system 920 may include any of the imaging systems described above. Treatment delivery system 900 may also include a digital processing system 930 to control radiation source 910, imaging system 920 and a patient support device such as a treatment couch 940. Digital processing system 930 may be configured to compare 2-D radiographic images from imaging system 920 and/or to register 2-D radiographic images from imaging system 920 from two or more stereoscopic projections, with digitally reconstructed radiographs (DRRs) generated by digital processing system 730 in diagnostic imaging system 700 and/or DRRs generated by processing device 810 in treatment planning system 800. Digital processing system 930 may include one or more general-purpose processors (e.g., a microprocessor), special purpose processor such as a digital signal processor (DSP) or other type of device such as a controller or field programmable gate array (FPGA). Digital processing system 930 may also include other components (not shown) such as memory, storage devices, network adapters and the like. Digital processing system 930 may be coupled to radiation source 910, imaging system 920 and treatment couch 940 by a bus 945 or other type of control and communication interface.

Digital processing system 930 may implement methods (e.g., such as methods 300 and 500 described above) to compare images obtained from imaging system 920 and/or to register images obtained from imaging system 920 with preoperative treatment planning images in order to align the patient on the treatment couch 940 within the treatment delivery system 900, and to precisely position the radiation source with respect to the target volume.

The treatment couch 940 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 940 may be a component of another mechanical mechanism, such as the Axum® treatment couch developed by Accuray, Inc. of California, or be another type of conventional treatment table known to those of ordinary skill in the art.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of a beam(s) and "target" may refer to a non-anatomical object or area.

It will be apparent from the foregoing description that aspects of the present invention may be embodied, at least in part, in software. That is, the techniques may be carried out in a computer system or other data processing system in response to its processor, such as processing device 810, for example, executing sequences of instructions contained in a memory, such as system memory 820, for example. In various embodiments, hardware circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller, such as processing device 810.

A machine-readable medium can be used to store software and data which when executed by a data processing system causes the system to perform various methods of the present invention. This executable software and data may be stored in various places including, for example, system memory 820 and storage 830 or any other device that is capable of storing software programs and/or data.

Thus, a machine-readable medium includes any mechanism that provides (i.e., stores and/or transmits) information in a form accessible by a machine (e.g., a computer, network device, personal digital assistant, manufacturing tool, any device with a set of one or more processors, etc.). For example, a machine-readable medium includes recordable/non-recordable media (e.g., read only memory (ROM); random access memory (RAM); magnetic disk storage media; optical storage media; flash memory devices; etc.).

It should be appreciated that references throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention. In addition, while the invention has been described in terms of several embodiments, those skilled in the art will recognize that the invention is not limited to the embodiments described. The embodiments of the invention can be practiced with modification and alteration within the scope of the appended claims. The specification and the drawings are thus to be regarded as illustrative instead of limiting on the invention.

What is claimed is:

1. A method, comprising:
acquiring data indicative of a motion of a target; and
determining, using a processing device, a timing for when to initiate one or more x-ray images based on the data indicative of the motion of the target, the determining comprising:
determining whether a position of the target, due to the motion, is within a treatment tolerance; and
generating the one or more x-ray images of the target if the position is not within the treatment tolerance.

2. The method of claim 1, further comprising:
computing the position of the target based on the one or more x-ray images.

3. The method of claim 2, further comprising:
directing a radiation treatment beam using the position of the target.

4. The method of claim 1, wherein the data comprises a prior x-ray image.

5. A treatment system, comprising:
an imaging apparatus comprising an x-ray source to generate one or more x-ray images;
a motion detecting apparatus to acquire data indicative of a motion of a target; and
a processing device coupled with the imaging apparatus and the motion detecting apparatus, wherein the processing device is configured to determine a timing for when to initiate the one or more x-ray images based on the data indicative of the motion of the target, wherein to determine the timing the processing device performs the following comprising:
determining whether a position of the target, due to the motion, is within a treatment tolerance; and
initiating the one or more x-ray images of the target if the position is not within the treatment tolerance.

6. The treatment system of claim 5, wherein the processing device is further configured to perform the following, comprising:
computing the position of the target based on the one or more x-ray images.

7. The treatment system of claim 6, further comprising:
a radiation delivery system operatively coupled with the processing device to deliver a radiation treatment beam to the target, wherein the processing device is further configured to direct the radiation treatment beam using the position of the target.

8. A non-transitory machine readable medium having instructions, that when executed by a processing device, cause the processing device to perform operations comprising:
acquiring data indicative of a motion of a target; and
determining, using a processing device, a timing for when to initiate one or more x-ray images based on the data indicative of the motion of the target, the determining comprising:
determining whether a position of the target, due to the motion, is within a treatment tolerance; and
generating the one or more x-ray images of the target if the position is not within the treatment tolerance.

9. The non-transitory machine readable medium of claim 8, wherein the instructions cause the processing device to perform further operations comprising computing the position of the target based on the one or more x-ray images.

10. The non-transitory machine readable medium of claim 9, wherein the instructions cause the processing device to perform further operations comprising directing a radiation treatment beam using the position of the target.

11. The method of claim 1, wherein determining the timing for when to initiate the one or more x-ray image comprises determining a timing between a plurality of x-ray images.

12. The treatment system of claim 5, wherein determining the timing for when to initiate the one or more x-ray image comprises determining a timing between a plurality of x-ray images.

13. The non-transitory machine readable medium of claim 8, wherein determining the timing for when to initiate the one or more x-ray image comprises determining a timing between a plurality of x-ray images.

* * * * *